(12) United States Patent
Thybo et al.

(10) Patent No.: US 9,822,904 B2
(45) Date of Patent: Nov. 21, 2017

(54) VALVE AND A METHOD OF OPERATING A VALVE

(71) Applicant: IMI HYDRONIC ENGINEERING INTERNATIONAL SA, Eysins (CH)

(72) Inventors: Claus Thybo, Sonderborg (DE); Anders Engelbrektsson, Boras (SE); Daniel Jilderos, Brämhult (SE)

(73) Assignee: IMI HYDRONIC ENGINEERING INTERNATIONAL SA, Eysins (CH)

( * ) Notice: Subject to any disclaimer, the term of this patent is extended or adjusted under 35 U.S.C. 154(b) by 0 days.

(21) Appl. No.: 15/105,216

(22) PCT Filed: Dec. 17, 2014

(86) PCT No.: PCT/EP2014/078300
§ 371 (c)(1),
(2) Date: Jun. 16, 2016

(87) PCT Pub. No.: WO2015/091690
PCT Pub. Date: Jun. 25, 2015

(65) Prior Publication Data
US 2016/0312916 A1  Oct. 27, 2016

(30) Foreign Application Priority Data
Dec. 20, 2013  (EP) ..................... 13199048

(51) Int. Cl.
*F16K 37/00* (2006.01)
*C07D 301/26* (2006.01)
(Continued)

(52) U.S. Cl.
CPC ........ *F16K 37/0083* (2013.01); *C07D 301/26* (2013.01); *F16K 1/12* (2013.01); *F16K 31/047* (2013.01)

(58) Field of Classification Search
CPC ...... F16K 37/0083; F16K 31/047; F16K 1/12; C07D 301/26
(Continued)

(56) References Cited

U.S. PATENT DOCUMENTS

| 4,347,195 A | 8/1982 | Ogawa |
| 5,931,374 A | 8/1999 | Knapp |

(Continued)

FOREIGN PATENT DOCUMENTS

| CA | 2 109 034 A1 | 4/1995 |
| CN | 101044313 A | 9/2007 |

(Continued)

OTHER PUBLICATIONS

Third Party Observation issued on Aug. 4, 2016, by the European Patent Office in corresponding European Patent Application No. 20130199048.3 (3 pages).

(Continued)

*Primary Examiner* — Marina Tietjen
(74) *Attorney, Agent, or Firm* — Buchanan Ingersoll & Rooney P.C

(57) ABSTRACT

The invention relates to a valve having a balancing function for a fluid distribution system. A valve closing member is movable between a closed position and a fully opened position. An actuation device is provided for changing the position of the valve closing member. A control unit is provided and comprises an electronic memory adapted to receive and store an opening limitation value, said opening limitation value being representative of a selected intermediate position between said closed position and said fully opened position of the valve closing member, wherein the control unit controls the actuation device to limit the movement of the valve closing member to positions from said closed position to said selected intermediate position. The (Continued)

invention also relates to a valve system and to a method of operating a valve.

7 Claims, 6 Drawing Sheets

(51) Int. Cl.
  *F16K 1/12* (2006.01)
  *F16K 31/04* (2006.01)
(58) Field of Classification Search
  USPC .................................................. 251/129.04
  See application file for complete search history.

(56) References Cited

U.S. PATENT DOCUMENTS

| | | | |
|---|---|---|---|
| 6,058,955 | A | 5/2000 | Griswold et al. |
| 6,382,226 | B1* | 5/2002 | Larson ............... F16K 37/0091 137/1 |
| 2008/0053528 | A1 | 3/2008 | Breda |
| 2009/0114861 | A1* | 5/2009 | Luebbers ................ F16K 3/03 251/129.11 |
| 2011/0114304 | A1 | 5/2011 | Keller |
| 2011/0127455 | A1 | 6/2011 | Hunnicutt |

FOREIGN PATENT DOCUMENTS

| | | |
|---|---|---|
| CN | 201428833 Y | 3/2010 |
| CN | 102164846 A | 8/2011 |
| CN | 202091558 U | 12/2011 |
| RU | 2144205 C1 | 1/2000 |
| WO | 2006/005167 A1 | 1/2006 |
| WO | WO 2012/002875 A1 | 1/2012 |

OTHER PUBLICATIONS

International Search Report (PCT/ISA/210) dated May 15, 2015, by the European Patent Office as the International Searching Authority for International Application No. PCT/EP2014/078300.
Written Opinion (PCT/ISA/237) dated May 15, 2015, by the European Patent Office as the International Searching Authority for International Application No. PCT/EP2014/078300.
"Characterised control valves (CCV) with adjustable flow rate and sensor-operated flow control," BELIMO, T5-P6 . . . W . . . E-MP, en, vol. 2.0, Dec. 2011, pp. 1-8 and 1-2.
"Dynamic Self Balancing Control Valve," FlowCon International, Sep. 2007, pp. 1-8.
"Dynamic Control Valve, Dynamic Self Balancing Control Valve, 15-40mm," FlowCon SM, Oct. 2007, pp. 1-5.
FlowCon SM, "The World's most Advanced Control Valves, Dynamic Temperature Control Valve" Jan. 2008, 3 pages.
Office Action dated Dec. 26, 2016, by the Chinese Patent Office in corresponding Chinese Patent Application No. 201480068407.6, (7 pages).
Office Action with Search Report (Decision to Grant) dated Jun. 20, 2017, by the Patent Office of the Russian Federation in corresponding Russian Patent Application No. 2016125886/06, and an English Translation of the Office Action with Search Report. (16 pages).

* cited by examiner

VALVE AND A METHOD OF OPERATING A VALVE

TECHNICAL FIELD

The present invention relates to a valve having a balancing function for a fluid distribution system, and to a valve system comprising such a valve. The present invention also relates to a method of operating a valve in a fluid distribution system.

BACKGROUND ART

Fluid distribution systems, for e.g. heating, cooling and water supply are designed to feed a fluid from a source to a consumption point. Each consumption point typically has a calculated and designed flow or differential pressure requirement. However, depending on the type of hydronic system, the flow requirement is often variable over time and can change with factors like seasonality (e.g. summer or winter), that changes the load from the consumption points, temperature changes of the system fluid, changes in consumption of the system fluid (e.g. for drinking water).

Control valves are frequently used in fluid distribution systems and have a variable opening such that the flow rates can be controlled.

Balancing and control valves provide an additional feature/function. To balance the system, a hand wheel of the valve is turned for presetting a maximum opening of the valve, i.e. a maximum flow through the valve. For instance, for a valve having a valve seat with which a movable valve disc is cooperateable, the mechanics coupled to the hand wheel will limit how far from the valve seat the valve disc is allowed to move. An actuator of the valve will notice that the valve cannot be opened more and a control part can therefore be calibrated to control the movement of the valve within the set limits.

While the presetting function provided by existing balancing and control valves is beneficial for obtaining desired flows in, for instance, different parts of a building, they have the drawback that they are relatively complex and costly compared to ordinary valves without the balancing function.

SUMMARY OF THE INVENTION

An object of the present invention is to provide a valve having a balancing function which alleviates the above mentioned drawbacks of existing valves. This and other objects, which will become apparent in the following, are accomplished by a valve, a valve system and a method of operating a valve as defined in the accompanying independent claims.

The present inventive concept is based on the insight that the existing hand wheels and complex mechanics for presetting maximum flow through the valve can be replaced by a virtual presetting.

According to a first aspect of the present inventive concept, there is provided a valve having a balancing function for a fluid distribution system.
The valve comprises
a fluid inlet and a fluid outlet,
a valve closing member movable between a closed position, in which fluid is prevented to flow from said fluid inlet to said fluid outlet, and a fully opened position,
an actuation device (such as electronic, pneumatic, hydraulic or mechanical) for changing the position of the valve closing member,
a control unit comprising an electronic memory adapted to receive and store an opening limitation value, said opening limitation value being representative of a selected intermediate position between said closed position and said fully opened position of the valve closing member,
wherein the control unit controls the actuation device to limit the movement of the valve closing member to positions from said closed position to said selected intermediate position.

Thus, the control unit with its electronic memory functions as a "virtual hand wheel". The valve may apart from its balancing function also have a control function. It may be designed as a balancing and control valve. The same control unit may be used both for the balancing function and for the control function. For instance, assuming the fully opened position of the valve closing member is 20 mm from its closed position and it is determined that for appropriate balancing a maximum opening would be 15 mm from the closed position, then an opening limitation value corresponding to 15 mm from closed position is stored in the electronic memory of the control unit. The control unit will thus recalibrate, such that the selected intermediate position (e.g. 15 mm from closed position) becomes the maximum allowable opening of the valve closing member. In other words, the control function of the control unit will only allow the valve closing member to move between the closed position (0 mm from closed position) to the selected intermediate position (e.g. 15 mm from closed position).

The recalibration can be exemplified as follows. Assuming that the valve controlling function of the control unit is based on an input voltage which may vary from 0 V to 10 V, wherein 0 V would result in the control unit controlling the actuation device to move the valve closing member to its closed position, and 10 V would result in the control unit controlling the actuation device to move the valve closing member to a maximum open position, and voltages there between would result in varying degrees of openness. Before the balancing/presetting has been done, the maximum open position is the fully opened position (20 mm in the example above). However, after presetting to an intermediate position (15 mm in the example above), the control unit will recalibrate so that an input of 10 V will result in the control unit controlling the actuation device to only move the valve closing member to said intermediate position, and not beyond.

From the above, it should be understood that the control unit may be operated to balance a fluid distribution system by presetting the working area for a subsequent controlling of the flow through the valve. Thus, said selected (desired) intermediate position may be regarded as a presetting of the Kv value, thus for flow control. The control unit may thus, in at least some exemplary embodiments, be regarded as having two operating modes, one for presetting/balancing and one for controlling.

The control unit may be commercially available control unit already used in valve applications. Examples of such control units are TA-MC-55, TA-MC55Y and TA-MC100, provided by TA Hydronics. The control unit may be updated with an appropriate printed circuit board and/or with appropriate software or the existing software may be reprogrammed for enabling an electronic memory. The opening limitation value can then be stored as a software value instead of a mechanical limitation. Thus, unlike the prior art, with the present inventive concept, the balancing/presetting, i.e. selecting a desired intermediate position to be a maximum allowable position, can be done without a need for someone to turn a hand-wheel. Furthermore, the complexity (and related costs) of the valve is reduced.

The valve closing member may be operated for regulating a physical property of the fluid. The physical property may, for instance, be the flow from the inlet to the outlet, the pressure drop from the inlet to the outlet, the Kv value and the temperature.

The inventive concept can be used for various types of valve closing member. For instance, the valve closing member could perform a rotating or pivoting movement, wherein the selected intermediate position would be at a rotational position between the closed and fully opened positions of the valve closing member. Examples of such rotating valves are ball valves and butterfly valves. In other embodiments, the valve closing member could perform a linear or translational movement. For instance, an the valve closing member may be attached or comprise a valve stem which may be lifted, suitably in an axial direction, from the closed position of the valve closing member to various opening degrees. Thus, the opening limitation value, which is representative of a selected intermediate position, may in this case be regarded as a lift limitation value.

According to a least one exemplary embodiment, a position determining means is operatively connected to the valve closing member for determining its current position and providing input about the current position to the control unit.

According to at least one exemplary embodiment, said actuation device comprises a motor for moving the valve closing member, and said position determining means is adapted to measure an actual position of the motor relative to a reference position of the motor, wherein the relationship between said actual position and said reference position is translatable to the current position of the valve closing member.

According to at least one exemplary embodiment, said actuation device is connected to a motor for moving the valve closing member, and said position determining means is adapted to measure an actual position of a component connected to the motor relative to a reference position of said component connected to the motor, wherein the relationship between said actual position and said reference position is translatable to the current position of the valve closing member.

The position determining means may be one or more of many conceivable options. For instance, the position determining means may be a positioning sensor, such as a magnetic, ultrasonic or optical sensor . The position determining means may also determine the position of the valve closing member indirectly. For instance, the movement of the valve closing member can be effected other moving devices, the motions of which may be converted to a movement of the valve closing member. Examples of such a device is a piston moving in a cylinder and being connected to the valve closing member by suitable linking. The position of the piston can be used to determine the position of the valve closing member. Another option would be in a variable volume chamber having a separating member, such as a flexible membrane or a movable piston, wherein the volume and/or the pressure in the chamber can be used for determining/calculating the position of the valve closing member. Another possibility, is to detect the rotational orientation of a drive shaft of the motor, e.g. detecting the position of one or more cogs of the drive shaft. Yet another option would be to use a stepper motor operatively connected to the valve closing member, wherein the number of steps taken from a reference position could be translatable to a position of the valve closing member.

With reference to a stepper motor, it is noted that according to at least one exemplary embodiment, said actuation device comprises or is connected to a stepper motor for moving the valve closing member, and said position determining means is adapted to count the number of steps taken by the stepper motor relative to a starting or reference position of the stepper motor, wherein the number of steps taken is translatable to the current position of the valve closing member. The translation may suitably be done by the control unit, however, the translation could be done by a remote calculating device, e.g. a control system or computer of a Building Management System (BMS). The BMS may send an input signal to the control unit, which input signal may include the number of steps to be taken, whereby the control unit sends an appropriate control signal to the stepper motor. Alternatively, the input signal includes information about the change in position of the valve closing member, and the control unit may calculate how many steps of the stepper motor corresponds to the change.

According to at least one exemplary embodiment, the valve comprises a gear and a motion converter, wherein the stepper motor is operatively connected to an input side of the gear and the motion converter is operatively connected to an output side of the gear, wherein the motion converter is operatively connected to the valve closing member for converting the motions of the gear to a movement of the valve closing member. The input side may suitably be a low torque side which is geared up to the output side/high torque side. A motion converter could thus convert rotary gear motion to a linear motion. For instance, a motion converter could comprise a spindle which comprises two mutually engaging threaded spindle parts. In other embodiments a motion converter could comprises a gear wheel engaging a rack gear.

According to at least one exemplary embodiment, the control unit is adapted to receive a balancing signal, such as an electronic balancing signal, representing said opening limitation value and/or said selected intermediate position. The electronic balancing signal may come from any one of several coneivable sources. For instance, the balancing signal may come from a flow measuring device operatively connectable to the control unit. Such a flow measuring device may, for instance, be connected to pressure ports of the valve. After adjusting the flow until flow measuring device has detected a desired maximum flow for balancing purposes, the flow measuring device may send the balancing signal to the control unit. This may be done via wires or wireless, e.g. via Bluetooth. The flow measuring device may have a user interface on which the user activates the transmission of the electronic balancing signal. Other conceivable solutions, would be that the flow measuring device is pre-programmed to detect a specic flow and once detected, it will automatically send the balancing signal to the control unit. As an alternative or complement to a flow measuring device for sending the balancing signal the valve itself may be provided with a user interface, such as a control panel or a push-button to send the balancing signal and thereby storing the opening limitation value. In other embodiments a user interface may be arranged in a remote position, such as at a control device of a BMS, at a dedicated control panel or arranged as a wireless communication device, such as a cell phone, computer or a remote control.

Once the balancing has been done and the control unit has been recalibrated, unless it was already correctly calibrated from a previous pre-setting, the control unit may be used to adjust the position of the valve to compensate for fluctuations or distortions in the fluid distribution system, or changes in other environmental conditions. For instance, if a certain temperature is desired in a room, and a window is opened letting in cool air, the control unit will control the actuating device to move the valve closing member to a larger degree of opening, whereby the flow of (heating) water increases and thereby increasing the heating emitted, for instance, from a radiator associated with the valve. This is reflected in at least one exemplary embodiment, wherein the control unit is adapted to receive a control signal for compensating for a difference between a measured value and a desired value of a physical property, such as temperature, pressure or flow. Said measured values may be captured by a temperature or a pressure sensor or a flow meter, respectively. The control signal could be an electronic signal, a pressure signal or other suitable signal.

According to at least one exemplary embodiment, the position determining means and/or the control unit is adapted to send an output signal to a feedback loop, the output signal being representative of the current position of the valve closing member, i.e. the signal contains information about the current position of the valve closing member, wherein the control unit is adapted to receive an input signal from the feedback loop for effecting a corrective movement of the valve closing member if the current position of the valve closing member deviates from a desired position of the valve closing member. Thus, the input signal could, for instance, be a control signal for compensating for deviations between desired and measured values of a physical property, as previously described. The feedback loop could be included in a Building Management System which communicates with a plurality of valves in a building or in other facilities.

It should be understood that the valve may have more than one inlet and one outlet. For instance, it may have two inlets and one outlet, or one inlet and two outlets, or two inlets and two outlets. It would also be conceivable to have more than two inlets and/or outlets.

It should also be understood that the fluid flowing through the valve may be a gas or a liquid, e.g. heating/cooling water or potable water. Thus, in accordance with at least one exemplary embodiment, valve is for a heating/cooling distribution system, such as a district heating/cooling system, or for a potable water distribution system.

According to a second aspect of the inventive concept, there is provided a valve system. The valve system comprises
a valve according to the first aspect of the inventive concept, and
a measuring device which is operatively connectable to the valve for measuring a physical property of the fluid the valve, wherein the measuring device comprises communicating means operatively connectable to the control unit of the valve for communicating at least one of the following pieces of information to the control unit:
said opening limitation value,
said selected intermediate position,
that a desired maximum opening is present in the valve, wherein the position of the valve closing member when said desired maximum opening is present becomes said selected intermediate position.

The valve may comprise pressure ports, to which the measuring device may be connected to determine the flow.

The measuring device may, for instance, be a flow measuring device for measuring the flow through the valve, and said desired maximum opening could be a desired maximum flow. The measuring device could also or alternatively measure the pressure or temperature of the fluid, depending on which physical property that is intended to be regulated.

According to a third aspect of the inventive concept, there is provided a method of operating a valve in a fluid distribution system. The method comprises
determining a desired maximum opening of the valve,
adjusting a valve closing member, which is movable between a closed position and a fully opened position, to an intermediate position in which said desired maximum opening is obtained,
storing in a control unit data representative of said intermediate position,
defining said intermediate position as being a maximum allowable opened position of the valve closing member.

The maximum opening could be based on a maximum desired flow, however, as described above, it could be based on other parameters depending on which physical property that is intended to be controlled with the valve at hand. Such physical properties may, for instance, be the pressure, differential pressure, flow and/or the Kv value.

The balancing or pre-setting of the valve may be done by using a flow and/or pressure measuring device as described above in relation to the first and second aspects. In the case of a flow measuring device, when it indicates or has found that the fluid flow through the valve is presently at a level of a previously chosen or calculated desired maximum flow, then the present intermediate position of the valve closing member is stored as data/software value in the control unit. Subsequently, the control unit may be operated to adjust and compensate for fluctuations or distortions in the fluid distribution system. The valve closing member is prevented by the stored value to move beyond said intermediate position. However, the valve closing member is still movable between the closed position and said intermediate position. This is reflected in the below exemplary embodiment.

According to at least one exemplary embodiment, the method further comprises providing an input signal to said control unit, which input signal represents a desired position between said closed position and said intermediate position, and moving the valve closing member to said desired position.

According to at least one exemplary embodiment, said input signal is a digital and/or analogous electrical input signal. In the case of a digital signal, it may be a data signal. Such data signal may be transmitted by wireless means of by wired means. An analogous electrical input signal could be an input current and/or a an input voltage.

According to at least one exemplary embodiment, said input signal comprises an input voltage to said control unit, said input voltage being variable between a predefined first voltage and predefined second voltage, wherein the degree of opening of the valve closing member is dependent on the value of said voltage, and wherein if said first voltage is received by the control unit, the control unit adjusts the valve closing member to its closed position, and if said second voltage is received by the control unit, the control unit adjusts the valve closing member to said intermediate position. The first voltage could, for instance, be 0 V. However, it would be conceivable for the first voltage to have a different value. The second voltage is suitable 100% of the maximum signal voltage for said input signal. However, other conceivable alternatives are also possible. For instance, the second voltage is less than 100% of the maximum voltage, wherein a higher voltage signal could be used to convey other information than information relating to the positioning of the valve closing member.

The input signal does not necessarily be conveyed as a voltage. It could be a wirelessly transmitted input signal. The input signal could instead of varying between two values, such as a first voltage and a second voltage, it could have a limited number of discrete values. For instance, the input signal could have a first value for opening and a second value for closing. In such case, as long as the input signal is received by the control unit, the valve closing member could be moved towards the opening and closing direction, respectively. When the input signal is stopped, the movement of the valve closing member is also stopped.

According to at least one example embodiment, the method further comprises determining the current position of the valve closing member, comparing said current position with a desired position of the valve closing member, making a corrective positioning of the valve closing member to compensate for the deviation between said current position and said desired position of the valve closing member.

According to at least one exemplary embodiment, movement of the valve closing member is actuated by a motor, wherein a movement of the valve closing member to a changed position comprises determining the displacement to be taken by the motor (or a component connected to the motor) for moving the valve closing member to said changed position, and providing a positioning signal from the control unit to the motor to preform said displacement.

According to at least one example embodiment, movement of the valve closing member is actuated by a stepper motor, wherein a movement of the valve closing member to a changed position comprises determining the number of steps to be taken by the stepper motor for moving the valve closing member to said changed position, and providing a positioning signal from the control unit to the stepper motor to take said number of steps.

Although the step of adjusting the valve closing member could be made by moving the valve closing member in the vicinity of what is believed will become the intermediate position, i.e. the position at which the desired maximum flow is obtained, in other embodiments, for initial calibration, the valve closing member is moved all the way from the closed position to the fully opened position and/or vice versa while measuring the opening degree.

According to at least one exemplary embodiment, said step of adjusting the valve closing member to an intermediate position comprises measuring a physical property (such as flow, Kv value, pressure, differential pressure, temperature and/or differential temperature) of the fluid in the valve and moving the valve closing member between said closed position and said fully opened-position, wherein said step of storing in a control unit data representative of said intermediate position is preceded by the step of sending a pre-setting signal to the control unit when said maximum desired opening has been reached.

In some instances, it may be desirable to change the pre-setting, i.e. to select a new intermediate position, and thus re-balancing the fluid distribution system. For instance, in winter time the selected intermediate position may be closer to the fully opened position than in summer time. This is reflected in at least one exemplary embodiment.

Thus, according to at least one exemplary embodiment, the method comprises at least two pre-setting modes, such as a winter mode and a summer mode, wherein in a first pre-setting mode said intermediate position is a first intermediate position between said closed position and said fully opened position, in a second pre-setting mode said intermediate position is a second intermediate position between said closed position and said fully opened position, wherein said first intermediate position is different from said second intermediate position.

In addition to what has been described above, it should be noted that the method according to the third aspect may include any of the embodiments and features described in connection with the first and second aspects.

DETAILED DESCRIPTION OF THE DRAWINGS

Figure 1:
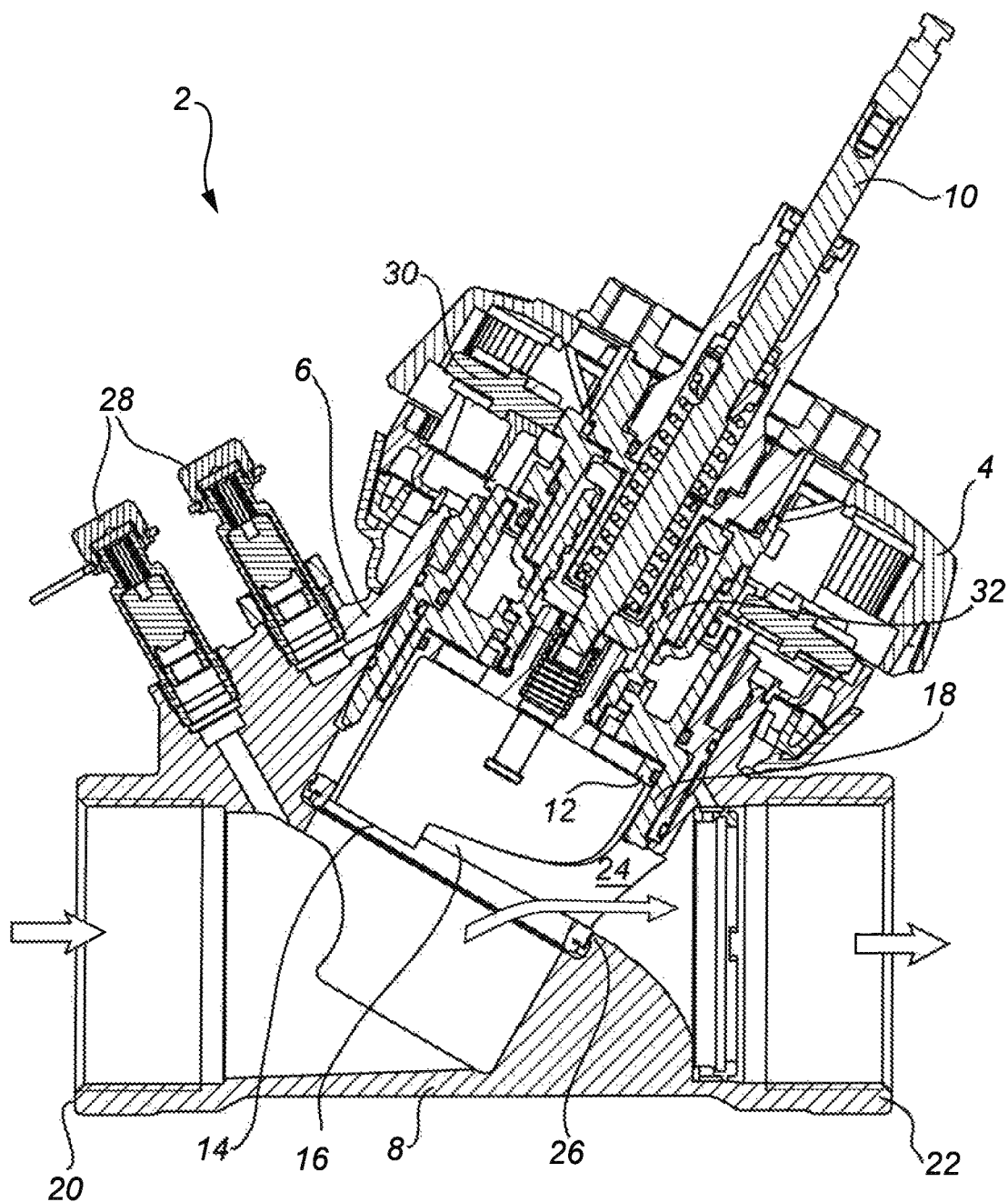
FIGS. 1 and 2 illustrate valves according to the prior art.
Figure 2:
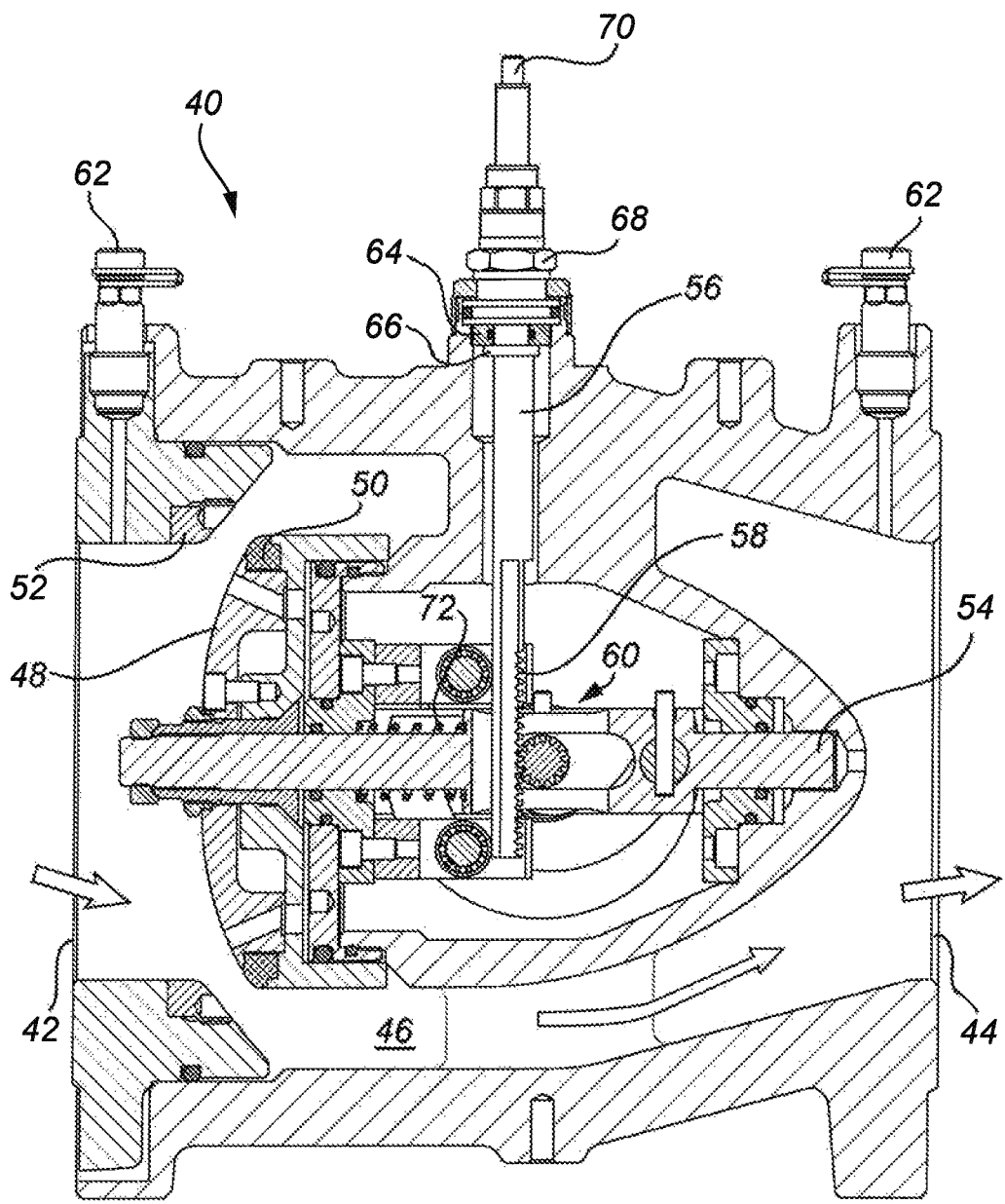

FIGS. 1 and 2 illustrate valves according to the prior art.

FIG. 1 illustrates a control valve 2 comprising a hand wheel 4. The actuator is arranged at a valve neck 6, which is connected to a valve body 8 of the control valve 2. A valve spindle 10 is centrically mounted in the valve neck 6. The valve neck 6 comprises a sleeve-shaped and cylindrical inner plug 12 for control and presetting of a desired maximum opening, in this case an optional Kvs value of the valve 2. The inner plug 12 is stationary relative to the valve spindle 10 and the inner plug 12 has an open bottom 14 for inflow of fluid and an opening 16 at its flank for outflow of fluid.

The valve neck 6 further comprises a sleeve-shaped and cylindrical outer plug 18, which partly surrounds the upper part of the inner plug 12. The outer plug 18 is provided, inter alia, for shutting off the opening 16 of the inner plug 12 to a desired opening area. The outer plug 18 is displaceably mounted in the valve neck 6, and moreover, for balancing, the inner plug 12 and the outer plug 18 are displaceable relative to each other.

The valve 2 also comprises an inlet connection 20 and an outlet connection 22. A flow through passage 24 is provided between the lower part of the valve neck 6 and a valve seat 26. The valve 2 also comprises two connections 28 for measuring nipples.

The fluid is enabled to flow through the valve 2 from the inlet 20 connection via the inner plug 12, inwards through its bottom 14 and outwards though its opening 16 at the flank, thereafter further through the flow through passage 24 and then to the outlet connection 22.

The hand wheel 4 is in engagement with a counter gear 30 provided with teeth, which in turn is in engagement with a preset screw 32. At the presetting the outer plug 18 is in its upper, relative the valve seat 26, farthest position. The presetting implies that the position/distance of the opening 16 of the inner plug 12 relative the valve seat 26 is set. A rotary motion of the hand wheel 4 is via the counter gear 30 transmitted to the presetting screw 32. The lower part of the presetting screw 32 is provided with an inner thread which cooperates with an outer thread provided at the upper part of the inner plug 12. The rotation of the presetting screw 32 is converted to an axial motion of the inner plug 12. In this way, the inner plug 12 is moved axially in a direction towards or away from the valve seat 26. It should be noted that the outer plug 18 is not moved during the presetting procedure, but stays in its upper position. When the presetting has been performed and the valve 2 is then ready for controlling, the relative position of the inner plug 12 and outer plug 18 given by the presetting, will remain unchanged. During controlling of the valve 2, as the inner and outer plugs 12, 18 move up or down, the opening 16 at the flank of the inner plug 12 will become shielded to greater or less extent by the valve seat 26. In the controlling of the valve 2, an actuator (not shown) is provided to push the upper end of the valve spindle 10 to move it downwardly and thus to move the inner and outer plugs 12, 18 downwardly against the bias of a spring.

FIG. 2 illustrates another prior art valve 40. The valve 40 has an inlet 42 and an outlet 44 and a fluid passage 46 therebetween. The fluid passage 46 may be sealed off by means of a plug 48 provided with a rubber element 50 when this is seated against a valve seat 52. The plug 48 is carried on a shaft 54 whose axis passes through the centre of the plug 48.

A stem 56 extends in a direction perpendicular to the motion of the plug 48 and parallel with the face of the plug in the form of a toothed portion 58. The toothed portion 58 is operatively connected to the shaft 54 via a gear and cam mechanism 60. An axial movement of the stem 56 is transformed into an axial movement of the shaft 54 (which is perpendicular to the movement of the stem 56). The plug 48, carried on the shaft 54, is thereby also moved axially adjusting the separation of the plug 48 and seat 52. The differential pressure across the valve 40 is monitored by using ports 62 on either side of the plug 48.

Similarly to the prior art valve 2 in FIG. 1, the maximum allowable opening of the valve 40 in FIG. 2 may also be preset. A mechanical stop 64 is present for limiting the movement of the stem 56. More specifically, when a circumferential flange 66 of the stem 56 comes into contact with the mechanical stop 64 the stem 56 cannot move further (upwards in FIG. 2). FIG. 2 illustrates the fully opened position of the valve 40. To preset the valve 40, a nut 68 is loosened and the mechanical stop 64 and the stem 56 are moved downwardly until the plug 48 is in a desired position, i.e. defining a maximum allowable opening of the valve 40. The nut 68 is then tightened, immobilizing the mechanical stop 64, wherein the presetting is completed. In subsequent controlling of the valve 40, an actuator (not shown) is provided to push the upper end 70 of the stem 56 to move it downwardly and thus to move the plug 48 towards the valve seat 52 against the bias of a spring 72. If no downward force is provided on the stem 56, the spring 72, being biased towards opening the valve, will cause an upward stroke of the stem 56, however, the stroke is limited by the mechanical stop 64.

Figure 3:
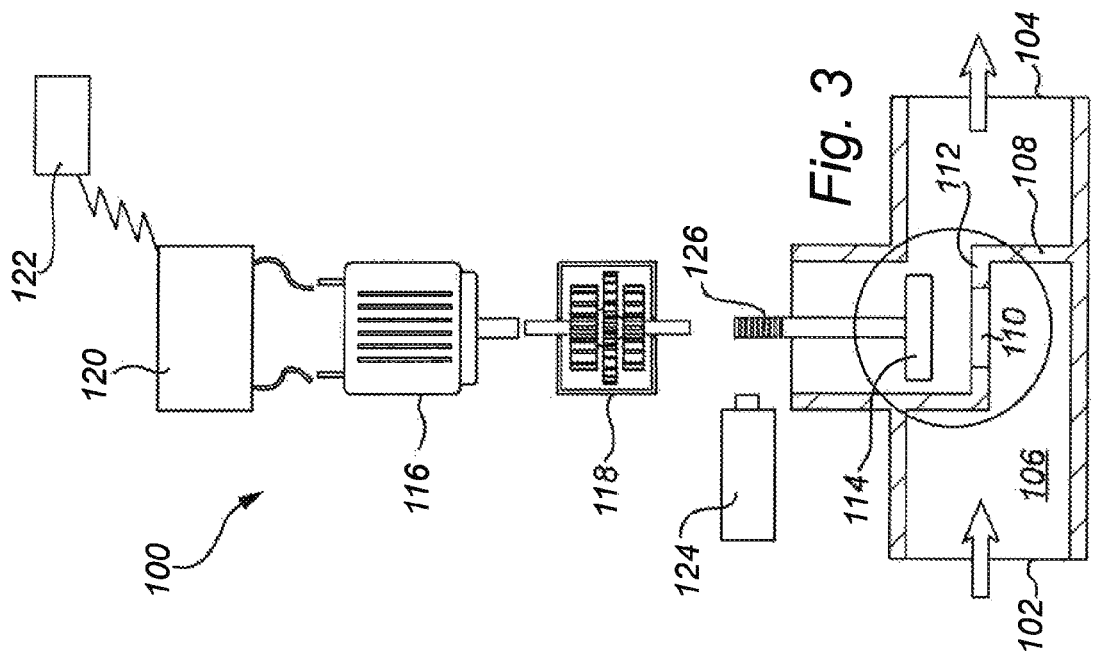
FIG. 3 illustrates schematically at least one an exemplary embodiment of the present inventive concept.

FIG. 3 illustrates schematically at least one an exemplary embodiment of the present inventive concept. It should be noted that FIG. 3 is a general schematic representation of a valve 100 having a balancing function and is merely intended to show an underlying principle of the inventive concept. However, this principle could be used on various types of valves, such as similar to those illustrated in FIGS. 1 and 2.

The valve 100 has a fluid inlet 102 and a fluid outlet 104, and a passage 106 between the inlet 102 and the outlet 104. In this embodiment, the valve 100 is illustrated as having a valve body with a partition wall 108 provided with a through-hole 110. An area around the through-hole 110 forms a valve seat 112. A valve closing member 114, in this embodiment illustrated as a plate carried by a valve stem, is adjustable in relation to the valve seat 112. The valve plate is operatively connected to an actuation device 116 for changing the position of the valve closing member 114. The actuation device 116 is herein illustrated as a motor. A gear mechanism 118 converts the rotational motion of the motor 116 to a linear motion of the valve closing member 114. A control unit 120 comprises an electronic memory which is adapted to receive and store an opening limitation value, which will now be further described with respect to FIGS. 4a-4d.

FIGS. 4a-4d illustrate detailed views of different positions of a valve closing member 114 in FIG. 3.

Figure 4A:
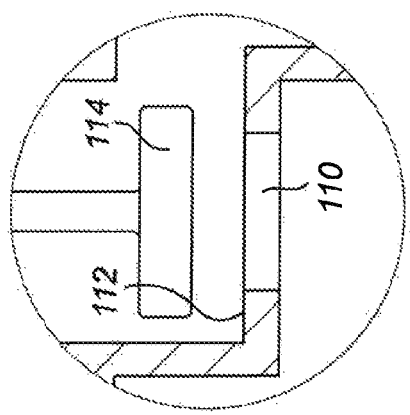
FIGS. 4*a*-4*d* illustrate detailed view of different positions of a valve closing member in FIG. 3.
Figure 4B:
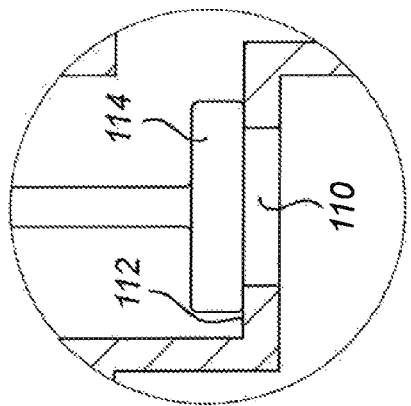
Figure 4C:
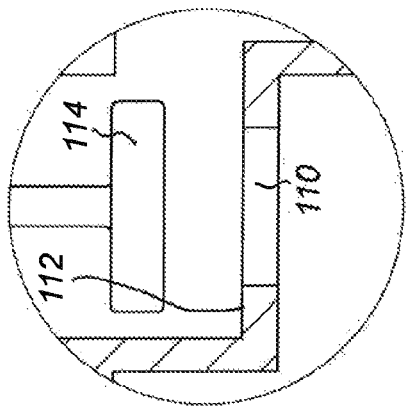
Figure 4D:
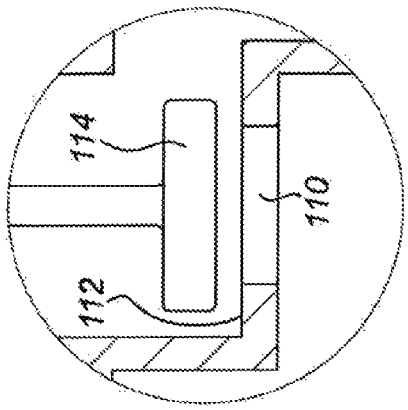

FIG. 4a illustrates a fully opened position of the valve closing member 114, i.e. the design maximum separation from the valve seat 112. FIG. 4d illustrates a closed position of the valve closing member 114, wherein the valve closing member 114 abuts the valve seat 112 to seal off the through-hole 110.

To balance the valve, a maximum desired opening of the valve is determined; such maximum desired opening being an intermediate position of the valve closing member 114, i.e. between the fully opened position in FIG. 4a and the closed position in FIG. 4d. For instance, FIG. 4b illustrates such an intermediate position. The selected intermediate position can be represented as an opening limitation value which is stored in the electronic memory of the control unit 120 (FIG. 3). The control unit 120 will then control the actuation device 116 to limit the movement of the valve closing member 114 so that it cannot be separated from the valve seat 112 beyond said intermediate position.

This selection of an intermediate position, i.e. the presetting of the valve 100, may be dependent on various parameters and/or operating conditions. For instance, during the different seasons of the year heating needs may vary in a building. As an example and for simplicity, assuming that a certain heating fluid is present in the system, having the same fluid temperature throughout the year, then FIG. 4b could represent said selected intermediate position in winter conditions, when more heating fluid is required, while FIG. 4c, in which the valve closing member 114 is closer to the valve seat 112, could represent said selected intermediate position during summer. However, in practice, the operating conditions may vary throughout the year, and for various reasons. The fluid temperature may for instance be different during different time periods. In practice, often a larger maximum allowable opening may be required for cooling purposes than for heating purposes. Thus, the schematic examples in FIGS. 4b and 4c, could depending on the particular operating conditions be reversed, i.e. 4b could represent an intermediate position when cooling is desired while FIG. 4c could represent an intermediate position when heating or less cooling is required.

In other words, the control unit 120 may be configured to change a stored opening limitation value when a new opening limitation value is received. In other embodiments, the control unit 120 may be configured to have several opening limitation values stored at the same time, wherein when a user selects a certain mode (e.g. winter or summer mode) the control unit 110 will use the corresponding opening limitation value to control the actuation device 116 so that the valve closing member 114 is prevented from moving beyond (to open more than) the intermediate position associated with said opening limitation value.

The balancing or presetting of the valve 100 may be done in various ways, as has been described elsewhere in this application. In FIG. 3, a Building Management System (BMS) 122 is schematically illustrated as being operatively in communication with the control unit 120. The BMS 122 may send an electronic balancing signal representing an opening limitation value and/or a selected intermediate position (which would be converted by the control unit to an opening limitation value for storage in the electronic memory).

FIG. 3 further illustrates a position determining means 124, herein illustrated as an optical or ultrasonic sensor which determines the current position of the valve closing member 114 and is adapted to provide feedback about the current position to the control unit 120. For illustrative purposes, the valve stem has been provided with level markings 126 which are detectable by the sensor 124. However, as mentioned elsewhere in this application, the position of the valve closing member 114 may be determined in various ways, such as monitoring the movement or position of cogs of a gear or counting the steps taken by a stepper motor, etc.

During operation, after the valve 100 has been balanced, and the opening limitation value has been stored by the electronic memory, the control unit 120 controls the valve. The position determining means 124, such as the one in FIG. 3 or a different one, and/or the control unit 120 is adapted to send an output signal to a feedback loop. The output signal contains information about the current position of the valve closing member 114, wherein the control unit 120 is adapted to receive an input signal from the feedback loop for effecting a corrective movement of the valve closing member 114 if the current position of the valve closing member deviates from a desired position of the valve closing member. Since an opening limitation value has been stored the control unit 120 has recalibrated such that an input signal representing "maximum opening" will not open to the fully open position in FIG. 4a, but only to the selected intermediate position (e.g. FIG. 4b).

This method of operating a valve 100 could be used in various types of fluid distribution systems, such as heating/cooling (e.g. district) distribution systems or potable water distribution systems.

Figure 5:
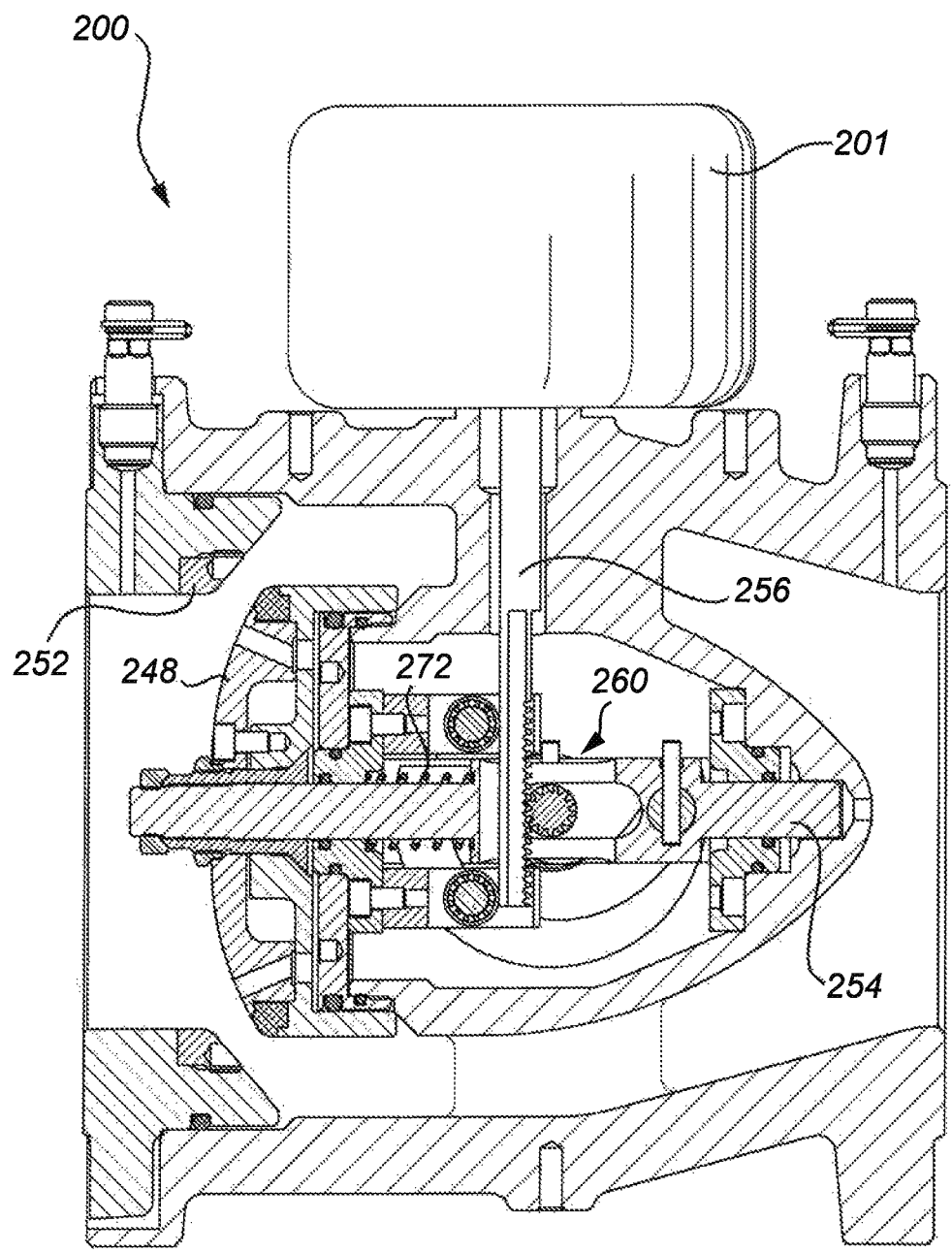
FIG. 5 illustrates a valve, partly in cross-section, according to at least one exemplary embodiment of the present inventive concept.

FIG. 5 illustrates a valve 200, partly in cross-section, according to at least one exemplary embodiment of the present inventive concept. The difference between this exemplary embodiment and the prior art valve 40 in FIG. 2 is in the presetting. Thus, the stem 256, cam mechanism 260, shaft 254, valve seat 252 and plug 248 (acting as a valve closing member) etc. may be the same (200 added to the reference numeral in FIG. 2) as in the prior art. However, the embodiment in FIG. 5 does not have a mechanical stop (c.f. the mechanical stop 64 in FIG. 2).

In FIG. 5 and in other embodiments, the movement of the valve closing member 248 is controlled by means of an electronic control arrangement 201. The electronic control arrangement 201 comprises a control unit and an actuation device (not shown), e.g. an electronic actuation device. In FIG. 5, the stem 256 is illustrated as being connected to the electronic control arrangement 201. To balance the valve 200, the electronic control arrangement 201 stores in an electronic memory of the control unit an opening limitation value. This may be provided in various ways, as already described in this application. For instance, when the valve closing member 248 is in such a position that a desired flow characteristics for balancing has been obtained, this intermediate position will be the new maximum allowable opening of the valve and this information will be stored in the electronic memory as an opening limitation value. In the subsequent control of the valve the control unit will control the actuation device so that it acts against the bias of the spring 272 so that the valve closing member 248 will not move away from the seat 252 any further than to said intermediate position.

Figure 6:
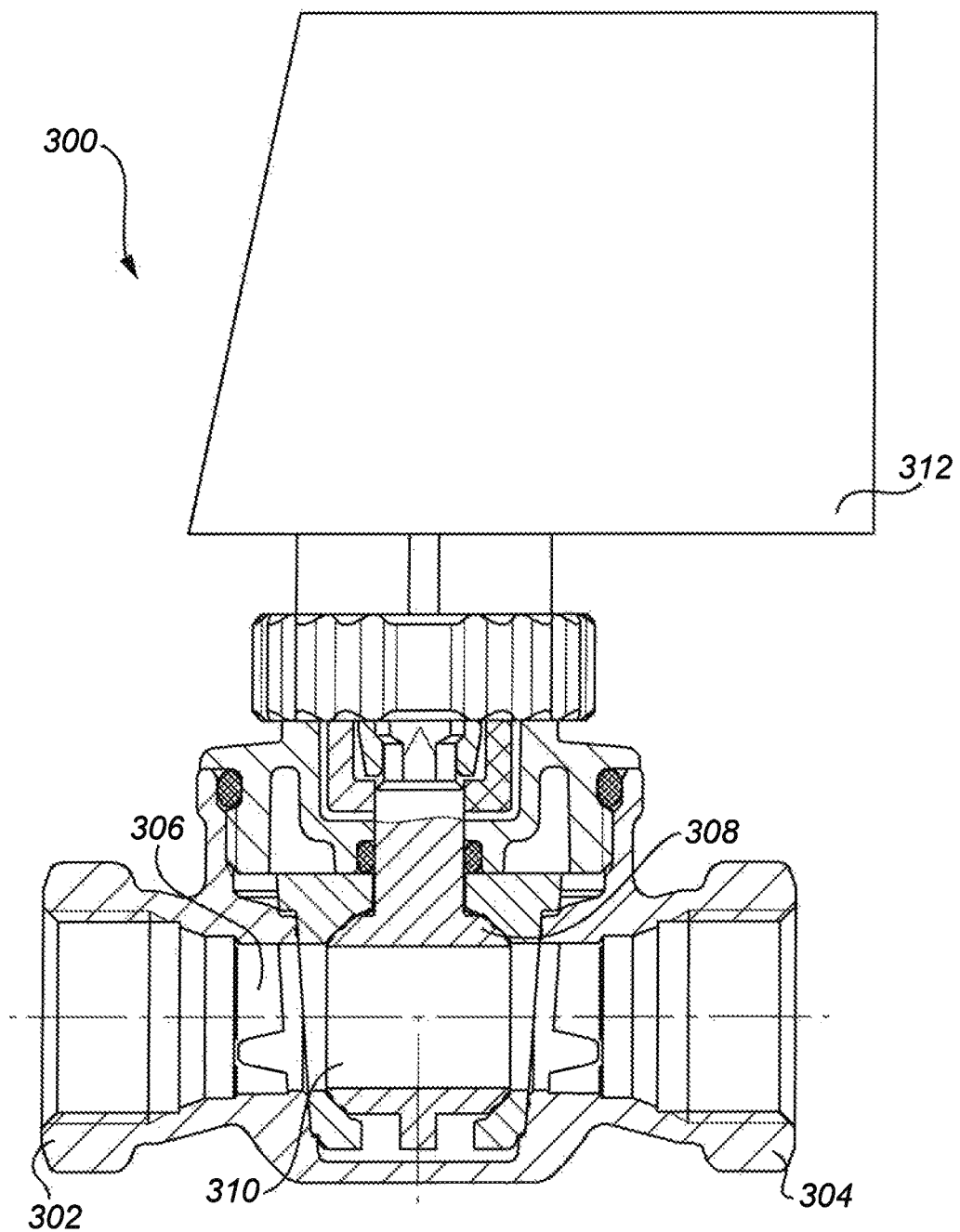
FIG. 6 illustrates a valve, partly in cross-section, according to at least a further exemplary embodiment of the present inventive concept.

FIG. 6 illustrates a valve 300, partly in cross-section, according to at least a further exemplary embodiment of the present inventive concept. The valve 300 has an inlet connection 302 and an outlet connection 304 and a flow passage 306 therebetween. The valve 300 comprises a rotating valve closing member 308. Here it is illustrated as a ball valve member 308. However, other possibilities could be a butterfly valve member or other suitable type of rotating valve members. In the ball valve member 308, a through-hole 310 is present. The through-hole 310 may be aligned to greater or less extent with the flow passage 306 to define an opening through the ball valve member 308. When the through-hole 310 is completely aligned with the flow passage 306 the ball valve member 308 is in its fully opened position. When the through-hole 310 faces a wall defining the flow passage 306 such that no fluid can flow through the ball valve member 308, it is in its closed position. Similarly to the description of the previous embodiments, a control unit may be provided (herein illustrated as forming part of an electronic control arrangement 312) to balance the valve 300. When the flow characteristics, such as the flow rate, is at a desired maximum allowable level, the rotational position of the ball valve member 308 will be stored as an opening limitation value in an electronic memory of the control unit. An actuation device (suitably also incorporated in the electronic control arrangement 312) will during operation of the valve be controlled by the control unit to allow the ball valve member 308 to rotate between its closed position and said rotational position which is stored as an opening limitation value (said rotational position being an intermediate position between the closed position and the fully opened position).

Figure 7:
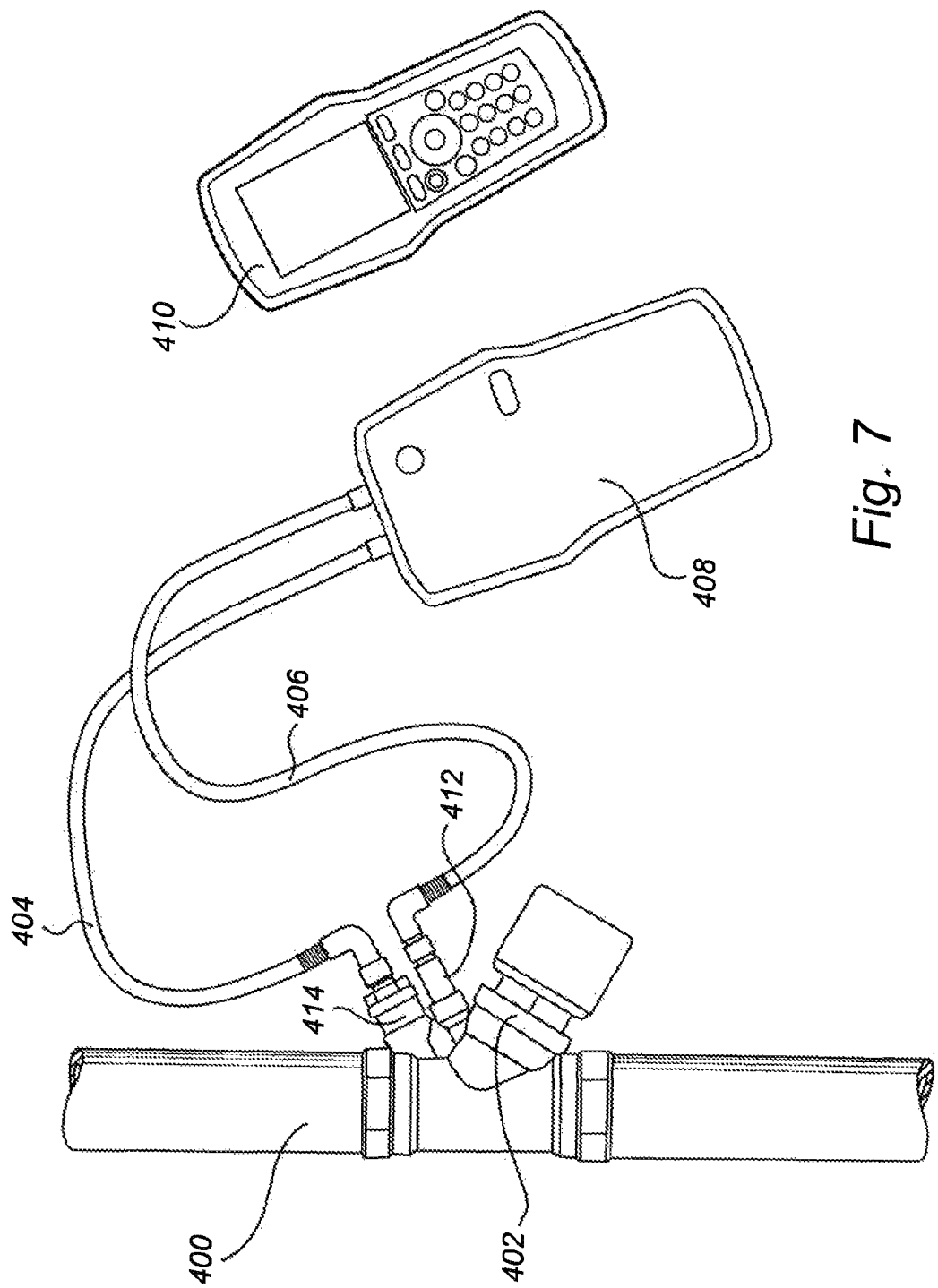
FIG. 7 illustrates a measuring device which is operatively connected to a valve according to at least one exemplary embodiment of the present inventive concept.

FIG. 7 illustrates a measuring device 408 which is operatively connected to a valve 402 according to at least one exemplary embodiment of the present inventive concept. The valve 402 is illustrated as being provided at a pipe 400 of a fluid distribution system. The valve 402 has two connections 412, 414 for connecting lines 404, 406, respectively, attached to the measuring device 408. By means of this arrangement the measuring device 408 acquires information about one or more physical properties of the valve 402 or of the fluid in the valve 402. Such physical properties may, for instance, be the flow, the pressure, the differential pressure, the Kv value, the temperature and/or the opening degree. When balancing/pre-setting the valve 402, a maximum opening could, for instance, be based on a maximum desired flow, and/or one or more of said other properties.

The measuring device 408 communicates wirelessly or by cable with a hand-held device 410, which gives information to an operator about the measured physical property and/or about a physical property calculated from the measured property. After a desired maximum opening of the valve 402 has been determined, the operator may, based on the measurements, adjust the valve closing member so that said maximum opening is obtained. When the hand-held device 410 shows that the fluid flow/differential pressure/Kv value etc. through the valve 402 is presently at a predefined maximum level, then the position of the valve closing member is stored as data/software value in the control unit (not shown), as previously described in this application. The hand-held device 410 may communicate said position (the intermediate position) to the control unit automatically when the predefined maximum level of the physical property has been reached, and/or an operator could actively instruct the hand-held unit to send the information to the control unit. Another possibility would be for a user to provide said information directly to the control unit, for instance, by means of a user interface at the control unit. Subsequently, the control unit may be operated to adjust and compensate for fluctuations or distortions in the fluid distribution system.

In each of the above described exemplary embodiments in FIGS. 3-7 and in other embodiments, after the presetting, i.e. after the opening limitation value has been stored, the control unit may receive an input signal containing information about a desired position between the intermediate position (stored as the opening limitation value) and the closed position of the valve closing member. The input signal could, for instance, be a control signal for compensating for deviations between desired and measured values of a physical property, as previously described. The signal could be digital, such as a data signal, or analoguous, such as a current or voltage signal. Due to the presetting, the control unit has been recalibrated based on the opening limitation value. Thus, the intermediate position will be considered as the functional 100% open position. Thus, an input signal requiring the valve to be 75% opened, will be interpreted as 75% of the openness of the intermediate position.

It should be understood that the inventive concept is not limited to the described exemplary embodiments; rather the scope being generally defined by the accompanying claims.

The invention claimed is:

1. A method of operating a valve in a fluid distribution system, comprising
   determining a desired maximum opening of the valve,
   adjusting a valve closing member, which is movable between a closed position and a fully opened position, to an intermediate position in which said desired maximum opening is obtained,
   after the adjusting, storing in a control unit data representative of said intermediate position,
   defining said intermediate position as being a maximum allowable opened position of the valve closing member.

2. The method according to claim 1, comprising
   providing an input signal to said control unit, which input signal represents a desired position between said closed position and said intermediate position, and
   moving the valve closing member to said desired position.

3. The method according to claim 2, wherein said input signal is a digital and/or analogous electrical input signal.

4. The method according to claim 1, comprising
   determining the current position of the valve closing member,
   comparing said current position with a desired position of the valve closing member,
   making a corrective positioning of the valve closing member to compensate for the deviation between said current position and said desired position of the valve closing member.

5. The method according to claim 1, wherein said step of adjusting the valve closing member to an intermediate position comprises measuring a physical property of the fluid in the valve, and moving the valve closing member between said closed position and said fully opened-position, wherein said step of storing in a control unit data representative of said intermediate position is preceded by the step of sending a pre-setting signal to the control unit when said maximum desired opening has been reached.

6. The method according to claim 1, comprising at least two pre-setting modes, wherein
   in a first pre-setting mode said intermediate position is a first intermediate position between said closed position and said fully opened position,
   in a second pre-setting mode said intermediate position is a second intermediate position between said closed position and said fully opened position,
   wherein said first intermediate position is different from said second intermediate position.

7. The method according to claim 5, wherein the physical property of the fluid in the valve including at least one of flow, Kv value, pressure, differential pressure, temperature and differential temperature, and the pre-setting signal is based on the measured physical property of the fluid in the valve.

* * * * *